(12) United States Patent
Grawe et al.

(10) Patent No.: US 6,974,885 B2
(45) Date of Patent: Dec. 13, 2005

(54) METHOD FOR ISOLATING PHARMACEUTICALLY EXPLOITABLE ETIDRONATE DISODIUM

(75) Inventors: Detlef Grawe, Kleinromstedt (DE); Barbara Schmidt, Gniebsdorf (DE); Harald Raethe, Jena (DE)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 10/381,535

(22) PCT Filed: Sep. 28, 2001

(86) PCT No.: PCT/DE01/03766

§ 371 (c)(1),
(2), (4) Date: Jun. 26, 2003

(87) PCT Pub. No.: WO02/26751

PCT Pub. Date: Apr. 4, 2002

(65) Prior Publication Data

US 2004/0024245 A1 Feb. 5, 2004

(30) Foreign Application Priority Data

Sep. 28, 2000 (DE) .......................... 100 49 735

(51) Int. Cl.⁷ .............................................. C07C 409/04
(52) U.S. Cl. ............................. 568/15; 568/10; 568/13; 568/15
(58) Field of Search .............................. 568/10, 13, 15; 562/20, 21, 22

(56) References Cited

U.S. PATENT DOCUMENTS

| | | | | |
|---|---|---|---|---|
| 3,400,149 A | * | 9/1968 | Quimby et al. | 562/22 |
| 3,497,313 A | * | 2/1970 | Quimby | 423/305 |
| 3,527,795 A | * | 9/1970 | Rose | 562/22 |
| 3,551,480 A | * | 12/1970 | Germscheid et al. | 562/22 |
| 3,855,284 A | * | 12/1974 | Henkel et al. | 562/22 |
| 4,269,828 A | * | 5/1981 | Flora et al. | 514/108 |
| 4,504,463 A | * | 3/1985 | Van Duzee | 424/1.77 |
| 6,143,923 A | * | 11/2000 | Shen et al. | 562/22 |

FOREIGN PATENT DOCUMENTS

| | | | |
|---|---|---|---|
| DE | 1 148 551 | | 5/1963 |
| GB | 1110987 | * | 4/1968 |
| GB | 2095 694 | * | 10/1982 |

OTHER PUBLICATIONS

CA:71:85354 abs of Calcified Tissue Research by Francis, Marion 3(2) pp 151–62 1969.*
CA:114:88545 abs of International Journal of Pharmaceutics by Bos et al 67(1) pp 39–49 1991.*
CA:85:130439 abs of Acta Pharmaceutica Technologica by Ehrhardt, L. 22(2) pp 109–19 1976.*
CA:103:196239 abs of DD 214609 Oct. 1984.*
CA:106:67494 abs of CS 223270 Sep. 1983.*
Blaser, B., et al: "1–Hysroxyalkane—1 . . . " Z. Anorg. Allg. Chem (1971), 381 (3), pp. 247–259.

* cited by examiner

*Primary Examiner*—Samuel Barts
*Assistant Examiner*—Lansana Nyalley
(74) *Attorney, Agent, or Firm*—Michael J. Striker

(57) ABSTRACT

The method of isolating an anhydrous etidronate disodium particulate includes preparing a liquid-liquid dispersion consisting of an aqueous-organic phase and an etidronate-disodium-salt-containing aqueous phase; adjusting a temperature of the liquid-liquid dispersion to between 0 and 30° C. and intensely agitating so that a coarse-particle fraction precipitates from the liquid-liquid dispersion, then drawing off a fine-particle suspension and allowing a fine-particle fraction to precipitate from it and filtering and drying the coarse particle fraction. In a preferred embodiment the fine-particle fraction is separated from the fine-particle suspension for recycling The resulting anhydrous etidronate disodium particulate has a grain size of from about 0.1 to 1 mm and a bulk density of 0.4 to 0.6 g/cm² with good properties for pharmaceutical applications.

12 Claims, 1 Drawing Sheet

METHOD FOR ISOLATING PHARMACEUTICALLY EXPLOITABLE ETIDRONATE DISODIUM

The invention relates to a method for isolating pharmaceutially exploitable etidronate disodium by precipitation in a liquid-liquid dispersion consisting of an aqueous-organic phase and an aqueous phase of the etidronate disodium salt, and to a new solid form of etidronate disodium obtainable by this method.

It is known from the technical and patent literature to prepare the disodium salt of hydroxyethane-1,1-diphosphonicacid (HEDP) by neutralization with sodium hydroxide solution in the presence of water (DE-A-1 148 551).

The prior-art isolation method for obtaining the solid has the following drawbacks:

- maximum water evaporation to obtain the anhydrous salt is possible only at relatively high temperatures;
- the spray-drying method for accomplishing this affords only a hygroscopic product of very low bulk density, high dust content and poor flowability which is thus not suitable for galenical use;
- although the alternatively usable thin-layer drying method gives compact structures at high temperatures, these structures are crusty and require an additional grinding process; and
- low-volatile impurities of HEDP, such as phosphorous acid and acetic acid, accumulate in the end product so that, for pharmaceutical purposes, an additional prepurification of HEDP is required (DD 275 462).

It is also known to prepare the disodium salt of HEDP by cooling crystallization from a concentrated solution. The drawbacks of this method are as follows:

- the voluminous crop of needle-shaped crystals is difficult to separate from the mother liquor;
- a felt-like filter cake is formed;
- on drying, the moist product agglomerates so that it is very difficult to remove the water from inside the agglomerates, and
- high mother liquor losses are incurred as a result of the high water solubility of the sodium salt.

Moreover, patent DE-A-1 148 551 describes the conversion of the acids and salts produced in crystalline form in the acylation of phosphorous acid into the corresponding alkali metal salts by precipitation induced by adding to the aqueous salt solution an organic solvent such as alcohol or acetone. This method has the following drawbacks:

- it affords products consisting of more or less fine or needle-shaped crystals which are also difficult to dry, because they, too, have a tendency to agglomerate and cake during the drying process;
- the end product contains a large amount of firmly held residual solvent, for example in the form of solvates and
- an additional product-grinding process is required.

It is also known from the technical literature that, as a rule, the addition of the aqueous salt solution to an organic solvent causes precipitation of a pasty and sticky aqueous phase which gradually solidifies into coarse lumps. This is due to the fact that the sodium salt is nearly insoluble in all organic solvents. A method of preparation or isolation of etidronate disodium having technical parameters permitting its pharmaceutical exploitation has not been published in the technical and patent literature.

The object of the invention is to provide a method for the production of pharmaceutically exploitable etidronate disodium, namely a method affording a high yield of high-purity product having a particle size of 0.2–1 mm, a bulk density of 0.4–0.6 g/cm$^3$ and good flowability and thus a product of high pharmaceutical exploitability.

According to the invention, this objective is reached by a method of isolation of etidronate disodium whereby a) a liquid-liquid dispersion consisting of
   an aqueous-organic phase and
   an aqueous, etidronate disodium-containing phase is adjusted to a temperature of 0 to 30° C. and intensely agitated,
b) a coarse-particle fraction is then caused to precipitate from the liquid-liquid dispersion, and
c) in a second, delayed step, a fine-particle fraction is caused to precipitate from the organic phase.

Preferably, in a step d), the fine-particle fraction is separated from the coarse-particle fraction by screening and is then recycled to the process.

In a further step e) following step d), the coarse-particle fraction can be filtered and dried in a fluidized bed to an end temperature of 85 to 100° C.

The liquid-liquid dispersion preferably contains a total amount of 25 to 35 vol. % of water and a total amount of etidronate disodium from 10 to 100 g/kg of dispersion.

The liquid-liquid dispersion is preferably adjusted to 5 to 10° C.

The aqueous-organic phase is preferably an isopropanol/water phase.

Furthermore, to form the liquid-liquid dispersion, it is preferable according to the invention to add an aqueous solution of etidronate disodium to an isopropanol/water solvent.

Another object of the present invention is etidronate disodium obtained according to the method of the invention. The etidronate disodium according to the invention is obtained in a form free of water of crystallization, it is predominantly amorphous and is characterized by the x-ray powder diagram shown in FIG. 1 and by the IR spectrum shown in FIG. 2.

Figure 1:
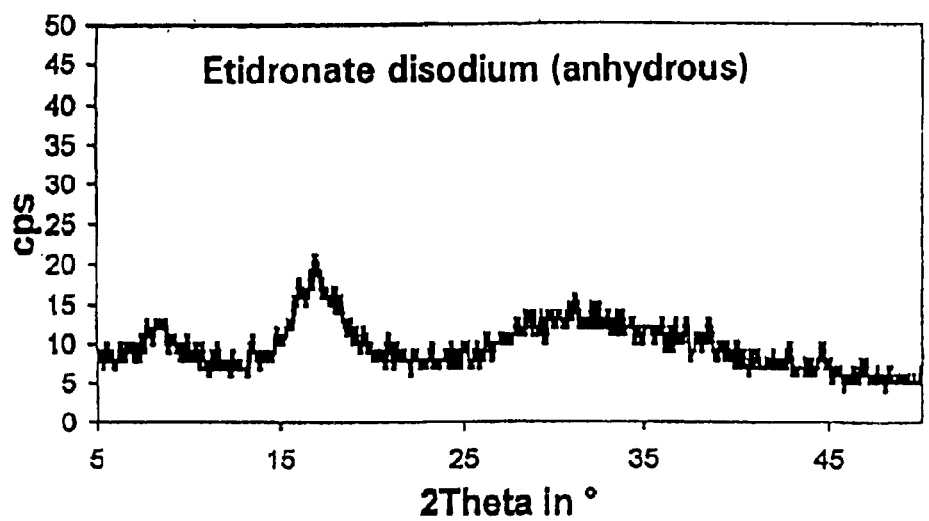
FIG. 1 represents an x-ray powder diagram of the etidronate disodium obtained by the method of the invention.

A preferred embodiment of the present invention is described by way of the following example.

In principle, the organic phase can consist of ethanol, methanol, acetone or isopropanol, the most favorable technical and product parameters being achieved by use of isopropanol. In the following, therefore, the method of the invention is described for isopropanol as the organic phase.

To prepare the liquid-liquid dispersion, an aqueous solution of etidronate disodium is added to a solvent consisting of an isopropanol/water mixture so as to achieve a total water content of 25 to 35 vol. % and in the suspension a solids content of 10 to 100 g/kg of dispersion. This liquid-liquid dispersion thus consists of a low-water isopropanol phase and a water-rich salt phase. A certain distribution equilibrium between water and the sodium salt is established between the two phases. Crucial for the precipitation process is that the organic phase removes water from the dispersed aqueous phase while picking up the salt to only a minor extent. Because of the high supersaturation, crystallization sets in suddenly after about 7 to 10 minutes. Agglomeration of the crystallizing droplets is superposed on this crystallization. This results in the formation of large particles which are broken up in the shearing field of the agitator resulting in the desired particle size distribution. With appropriate agitation energy, this mechanical comminution is possible only during a few minutes in the transition range from the still liquid to the solid state.

In the organic phase, a fraction of needle-shaped fine particles precipitates in small amount and in somewhat delayed fashion relative to the afore-described coarse-particle precipitation. Because of its substantially lower sedimentation rates it is rapidly and readily screened off before the solid-liquid separation and is recycled to the process. The sandy coarse-particle fraction is then filtered and washed. By vacuum drying in a fluidized bed, the salt is dried by gradually increasing the temperature to about 85 to 100° C. This gives the anhydrous salt.

An essential result of the use of the method of the invention is that it permits the production of pharmaceutically exploitable etidronate disodium. The advantage of this approach was that a method was developed which is characterized by the following.

- It permits the production of nearly dust-free etidronate disodium from a liquid-liquid dispersion having a total water content of 25 to 35 vol. % and a total etidronate disodium salt content of 10 to 100 g/kg of dispersion. The etidronate disodium has a particle size of 0.2 to 1.0 mm and possesses other solids properties that are advantageous for the subsequent tabletting, for example a bulk density of 0.4–0.6 g/cm$^3$ and the fact that the particle size distribution of etidronate disodium shows a maximum of 10 wt. % of all particles as being >1 mm and a maximum of 5 wt. % of all particles as being <0.1 mm. An etidronate disodium tablet consists mostly of the active substance. The tablet properties are thus determined to a high degree by the solids properties of the active substance.
- It affords an etidronate disodium that meets the pharmaceutical purity requirements of the US Pharmacopeia [USP].
- It provides a product that retains its sandy consistency during the drying process and that can readily be dried to obtain the anhydrous form.

During the drying phase, namely the liberation of the water of crystallization, in particular, this is of crucial importance if a uniformly dried product is to be obtained. Moreover, the drying process is not burdened by the separation of large quantities of fine dust from the water vapor generated by the drying of the hydrate.

Moreover, as a result of this method and the distribution equilibrium associated therewith in the liquid-liquid dispersion system, the contaminants of HEDP (phosphorous acid and acetic acid) end up to an extent of 95% and 99%, respectively, in the organic phase and not, as expected, preferably in the aqueous phase. Thus, these impurities do not precipitate together with the end product.

For additional advantages, the reader is referred to the description of the practical examples.

The invention will now be illustrated by way of the following preferred non-limiting examples.

Methods of Measurement

X-Ray Powder Diffraction: XRPD

The data were obtained with a Siemens D 5000 diffractometer with a Cu anode (resolution: 0.01° between $5° \leq 2\theta \leq 50°$).

IR Spectroscopy

An ATI Mattson, Genesis FT-IR was used with KBr, 8 t, 90 sec.

Particle Size Analysis

A RETSCH screen analysis system was used.

Bulk Density Determination

Bulk density was determined by means of a graduated cylinder (unshaken).

Water Content

The loss on drying was determined with a Mettler-Toledo moisture determination device, 200° C., 20 minutes.

Acetic Acid

The acetic acid content was determined by gas chromatography (GC headspace, DB5, 30 m, FID).

Isopropanol

The isopropanol content was determined by gas chromatography (GC headspace, DB wax, 30 m, FID).

Phosphite

The phosphite content was determined by iodometric titration.

EXAMPLE 1

10.5 L of isopropanol containing 25 vol. % of water and precooled to −7° C. was charged to an agitated vessel equipped with a turbine agitator and two baffles. While agitating, 1.7 L of an aqueous solution of the sodium salt and having a concentration of 350 g/L was added rapidly. The solution contained 0.6 wt. % of phosphorous acid and 0.6 wt. % of acetic acid. After about 3 to 4 min, the rotational speed was adjusted to 650 to 700 rpm, and the mixture was allowed to agitate at this speed for 10 minutes. The rotational speed was then reduced to about 250 to 300 rpm, and the mixture was allowed to agitate for an additional 10 minutes. The agitation was discontinued which caused sedimentation of the coarse-particle fraction to occur within 3 minutes. The supernatant fine-particle suspension was drawn off, the coarse-particle sediment was washed with 7 L of isopropanol/water mixture (25 vol. % of water or clear mother liquor from previous precipitation cycles) by brief agitation, and the supernatant suspension was then again drawn off. In this manner, the fine-particle fraction was separated almost completely. The fine-particle fraction amounted to about 18 to 19% of the solid material. The coarse-particle fraction was filtered and dried in a stream of air.

The moist product was dried in a rotational evaporator under vacuum. After attaining a vacuum of 2 kPa, the heating bath temperature was gradually increased to 80° C. within a period of 3 hours. Under these conditions, under a vacuum of 2 to 3 kPa, the free moisture was essentially removed from the fluidized bed. The vapor was condensed. Then, within a period of 3 hours, the water of crystallization was removed from the fluidized bed under a vacuum of less than 2 kPa and at a heating bath temperature of 100° C.

This gave an end product having the following particle size distribution.

| 0.1 | mm | 0.07% |
|---|---|---|
| 0.1–0.2 | mm | 23.8% |
| 0.2–0.5 | mm | 27.3% |
| 0.5–0.8 | mm | 46.2% |
| 0.8–1.0 | mm | 2.16% |
| 1.0 | mm | 0.47% |

The bulk density was 0.48 g/cm$^3$.

The following additional quality parameters were attained.

|  |  |  |
|---|---|---|
| Concentration: |  | 100% |
| Drying losses: |  | 3.5% |
| Phosphites: |  | 0.06% |
| Isopropanol: |  | 0.01% |
| Acetic acid: |  | 0.01% |

The mother liquor was separated from the fine-particle suspension by sedimentation and distillation. At the end, this gave an aqueous solution which can be reused for precipitation. The clear mother liquors, washing mixtures and screening mixtures were partly reconstituted and again used for screening or they were separated by simple distillation into an isopropanol/water mixture and an aqueous still residue containing the HEDP impurities. The yield of solids, taking into account the fine-particle recycling, was 97% of the theoretical.

EXAMPLE 2

The method was the same as in Example 1 with the exception that the water content of the isopropanol used was 22 vol. %. The screened-off fine-particle fraction amounted to about 14 to 15% of the solids. The end product obtained had the following particle size distribution.

| | | |
|---|---|---|
| 0.1 | mm | 0.0% |
| 0.1–0.2 | mm | 0.07% |
| 0.2–0.5 | mm | 19.7% |
| 0.5–0.8 | mm | 54.9% |
| 0.8–1.0 | mm | 15.6% |
| 1.0 | mm | 9.71% |

The bulk density was 0.51 g/cm$^3$.

EXAMPLE 3

The method was the same as in Example 1 with the exception that a sodium salt solution containing 3 wt. % of phosphorous acid was used.

This gave an end product of the following quality.

| | | |
|---|---|---|
| Concentration: | | 100% |
| Drying losses: | | 3.5% |
| Phosphites: | | 0.61% |
| Isopropanol: | | 0.01% |
| Acetic acid: | | 0.01% |

What is claimed is:

1. An anhydrous etidronate disodium solid particulate consisting of anhydrous etidronate disodium and having a grain size of 0.1 to 1 mm and a bulk density of 0.4 to 0.6 g/cm$^2$.

Figure 2:
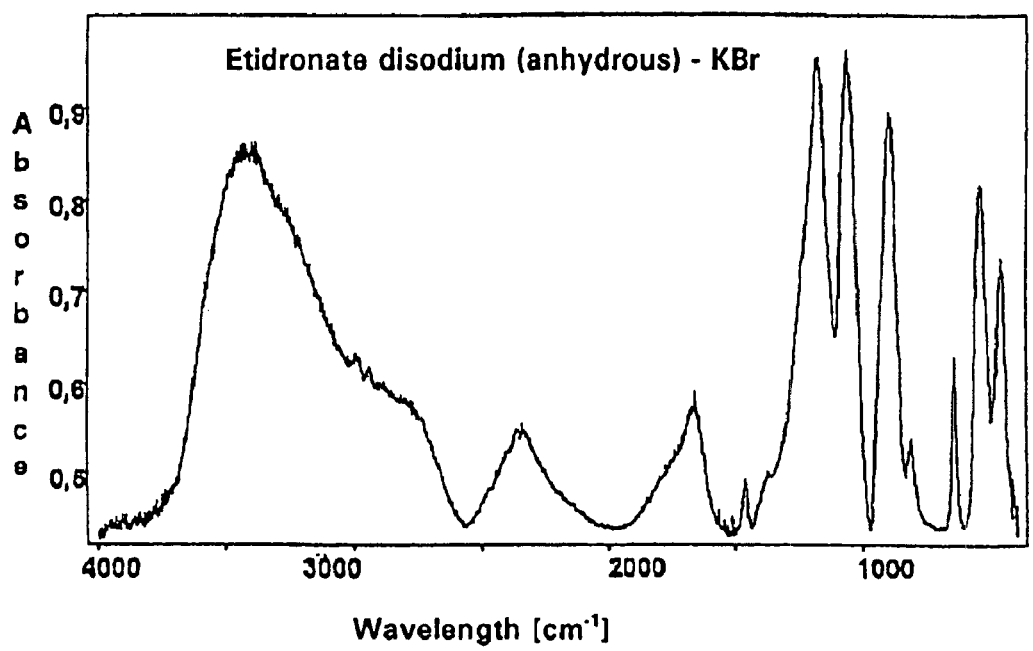
FIG. 2 represents an IR spectrum of etidronate disodium obtained by the method of the invention.

2. An anhydrous etidronate disodium solid particulate consisting of anhydrous etidronate disodium and having a grain size of 0.1 to 1 mm and a bulk density of 0.4 to 0.6 g/cm$^2$, and wherein said anhydrous etidronate disodium is characterized by an X-ray powder diffractogram as shown in FIG. 1 and an IR spectrum as shown in FIG. 2.

3. The solid particulate as defined in claim 1, wherein said anhydrous etidronate disodium is predominantly amorphous.

4. A method of isolating an anhydrous etidronate disodium solid particulate, said method comprising the steps of:
    a) preparing a liquid-liquid dispersion consisting of an aqueous-organic phase and an etidronate-disodium-salt-containing aqueous phase, wherein said etidronate-disodium-salt-containing aqueous phase comprises etidronate disodium and water and said aqueous-organic phase consists of water and isopropanol, said liquid-liquid dispersion having a total water content of about 25 to 35 percent by volume and containing from about 10 to 100 g of said etidronate disodium per kilogram of said dispersion;
    b) adjusting a temperature of said liquid-liquid dispersion to between 0 and 30° C. and intensely agitating said liquid-liquid dispersion, so that a coarse-particle fraction precipitates from the liquid-liquid dispersion;
    c) after the adjusting and the agitating, drawing off a fine-particle suspension and allowing a fine-particle traction to precipitate delayed in relation to precipitation of said coarse-particle fraction from the liquid-liquid dispersion; and
    d) filtering and drying the coarse particle fraction in a fluidized bed to a final temperature of 85° C. to 100° C. to obtain said anhydrous etidronate disodium, solid particulate;
    so that said anhydrous etidronate disodium solid particulate consists of anhydrous etidronate disodium and has a grain size of from 0.1 to 1 mm and a bulk density of from 0.4 to 0.6 g/cm$^2$.

5. The method as defined in claim 4, wherein said temperature of said liquid-liquid dispersion after said adjusting is from 5 to 10° C.

6. The method as defined in claim 4, wherein said fine-particle traction is separated from said fine-particle suspension for recycling.

7. The method as defined in claim 4, wherein, prior to the filtering and the drying, the coarse-particle fraction is washed with an isopropanol/water mixture with agitation and a supernatant residual suspension is drawn off, so as to more completely separate fines.

8. A method of isolating an anhydrous etidronate disodium solid particulate, said method comprising the steps of:
    a) preparing a liquid-liquid dispersion consisting of an aqueous-organic phase and an etidronate-disodium-salt-containing aqueous phase, wherein said etidronate-disodium-salt-containing aqueous phase comprises etidronate disodium and water and said aqueous-organic phase consists of water and an organic solvent, said liquid-liquid dispersion having a total water content of 25 to 35 percent by volume and containing from 10 to 100 g of said etidronate disodium per kilogram;
    b) adjusting a temperature of said liquid-liquid dispersion to between 0 and 30° C. and intensely agitating said liquid-liquid dispersion, so that a coarse-particle fraction precipitates from the liquid-liquid dispersion;
    c) after the adjusting and agitating, drawing of a fine-particle suspension and allowing a fine-particle traction to precipitate delayed in relation to precipitation of said coarse-particle fraction from the liquid-liquid dispersion; and
    d) filtering and drying the coarse particle fraction in a fluidized bed to a final temperature of 85° C. to 100° C. to obtain said anhydrous etidronate disodium solid particulate;
    so that said anhydrous etidronate disodium solid particulate consists of anhydrous etidronate disodium and has a grain size of from about 0.1 to 1 mm and a bulk density of from 0.4 to 0.6 g/cm².

9. The method as defined in claim 8, wherein said organic solvent consists of isopropanol or ethanol.

10. The method as defined in claim 8, wherein said temperature of said liquid-liquid dispersion after said adjusting is from 5 to 10° C.

11. The method as defined in claim 8, wherein said fine-particle fraction is separated from said fine-particle suspension for recycling.

12. The method as defined in claim 4, further comprising pre-cooling 10.5 L of a mixture of said isopropanol and said water containing 25% by volume of said water to −7° C. and then agitating said mixture of said isopropanol and said water with 1.7 L of an aqueous salt solution containing 350 g of said etidronate disodium per liter, in order to form said liquid-liquid dispersion.

* * * * *